United States Patent [19]

Merger et al.

[11] Patent Number: 4,963,672
[45] Date of Patent: Oct. 16, 1990

[54] PREPARATION OF CAPROLACTAM

[75] Inventors: Franz Merger, Frankenthal; Rolf Fischer, Heidelberg; Wolfgang Harder, Weinheim; Claus-Ulrich Priester, Ludwigshafen; Uwe Vagt, Speyer, all of Fed. Rep. of Germany

[73] Assignee: BASF Aktiengesellschaft, Ludwigshafen, Fed. Rep. of Germany

[21] Appl. No.: 448,899

[22] Filed: Dec. 12, 1989

[30] Foreign Application Priority Data

Dec. 24, 1988 [DE] Fed. Rep. of Germany ....... 3843791

[51] Int. Cl.$^5$ .......................................... C07D 201/08
[52] U.S. Cl. .................................................... 540/538
[58] Field of Search ......................................... 540/538

[56] References Cited

U.S. PATENT DOCUMENTS

| 4,250,093 | 2/1981 | Pesa et al. | 260/239.3 A |
| 4,356,124 | 10/1982 | Pesa et al. | 260/326.5 FN |
| 4,730,040 | 3/1988 | Vagt et al. | 540/538 |
| 4,730,041 | 3/1988 | Hutmacher et al. | 540/538 |
| 4,731,445 | 3/1988 | Hutmacher et al. | 540/538 |
| 4,767,857 | 8/1988 | Merger et al. | 540/538 |

Primary Examiner—Robert T. Bond
Attorney, Agent, or Firm—Keil & Weinkauf

[57] ABSTRACT

Caprolactam is prepared in a process comprising the following steps:
(a) reacting the 5-formylvaleric ester with liquid ammonia as reaction medium and hydrogen in the presence of a ruthenium catalyst in liquid phase at from 80° to 140° C. under a hydrogen partial pressure of from 40 to 100 bar,
(b) replacing the reaction medium ammonia by an aromatic hydrocarbon having a boiling point of from 80° to 240° C. which is liquid under the reaction conditions,
(c) heating the resulting mixture in liquid phase under superatmospheric pressure at 230°–350° C. to form caprolactam, and
(d) isolating caprolactam from the resulting reaction mixture.

17 Claims, No Drawings

PREPARATION OF CAPROLACTAM

The present invention relates to a process for preparing caprolactam from 5-formylvaleric esters.

DE-A-No. 3,602,376 discloses a process for preparing caprolactam wherein a 5-formylvaleric ester is reacted with excess ammonia and hydrogen in the presence of a hydrogenation catalyst under superatmospheric pressure at from 40° to 130° C. using an alkanol as reaction medium, the ammonia and hydrogen are then removed, and the resulting reaction mixture is then heated to 150°-250° C. This process has the disadvantage that the yields are in need of improvement and that, furthermore, in the cyclization stage, the conversion of 6-aminocaproic ester leaves something to be desired, so that major quantities of the thermally unstable 6-aminocaproic ester need to be recycled.

DE-A-No. 3,602,375 discloses a process for preparing caprolactam wherein a 5-formylvaleric ester is reacted with excess ammonia and hydrogen in the presence of a hydrogenation catalyst under superatmospheric pressure at from 40° to 130° C. using an alkanol as reaction medium, the ammonia and hydrogen are removed, and the reaction mixture thus obtained is reacted at elevated temperature with water by simultaneous removal of alkanol and then heated to 150°-370° C. to form caprolactam. This process has the disadvantage that major amounts of alkanol need to be separated off by distillation. In addition, the yields are in need of improvement.

Finally, DE-A-No. 3,602,377 discloses a process for preparing caprolactam wherein the 5-formylvaleric ester is initially hydrolyzed with water in the presence of a catalyst from 30° to 200° C. to 5-formylvaleric acid which is reacted with ammonia and hydrogen in the presence of a solvent and hydrogenation catalyst under a superatmospheric pressure at from 50° to 150° C. to give 6-aminocaproic acid, the ammonia and the catalyst are separated off, and the resulting solution of 6-aminocaproic acid is heated to 150°-370° C. to form caprolactam. For this process to be practised in industry, the yields must be improved. Moreover, this process requires an additional hydrolysis stage.

It is an object of the present invention to provide a process for preparing caprolactam starting from a 5-formylvaleric ester in a technically simple manner under high conversions, selectivities and space-time yields with minimal by-product formation.

We have found that this object is achieved by a process for preparing caprolactam by reacting a 5-formylvaleric ester with excess ammonia and hydrogen in the presence of a hydrogenation catalyst at elevated temperature under superatmospheric pressure in a reaction medium and cyclizing the resulting 6-aminocaproic ester at elevated temperature, comprising the steps (a) reacting the 5-formylvaleric ester with liquid ammonia as reaction medium and hydrogen in the presence of a ruthenium catalyst in liquid phase at from 80 to 140° C. under a hydrogen partial pressure of from 40 to 100 bar, (b) replacing the reaction medium ammonia by a liquid aromatic hydrocarbon having a boiling point of from 80° to 240° C. which is inert under the reaction conditions, (c) heating the resulting mixture in liquid phase under superatmospheric pressure at 230°-350° C. to form caprolactam, and (d) isolating caprolactam from the resulting reaction mixture.

The novel process has the advantage that there is no need to use an alkanol as reaction medium. It further has the advantage that the hydrogenation stage proceeds with high weight hourly space velocities over the catalyst, which has a long life, and thus with high spacetime yields. The novel process has the further advantage of low by-product formation.

Preferred starting materials are alkyl, in particular $C_1$-$C_4$-alkyl, 5-formylvalerates. Suitable starting compounds are for example methyl, ethyl, propyl, isopropyl and n-butyl 5-formylvalerates. Industrially, methyl 5-formylvalerate is particularly important.

In stage a, the reaction is carried out in liquid ammonia, which functions not only as reactant but also as solvent. In general, from 1 to 6 kg, preferably from 1.2 to 3.6 kg, in particular from 1.2 to 2.4 kg, of ammonia are used per kg of 5-formylvaleric ester. The reaction is carried out at 80°-140° C., advantageously at 100°-135° C., in particular at 110°-130° C.

Advantageously, from 1 to 20 moles of hydrogen are used per mole of 5-formylvaleric ester. The hydrogen is kept under a partial pressure of from 40 to 1000 bar, preferably from 50 to 500 bar, in particular from 70 to 200 bar.

According to the invention, the catalyst used is ruthenium. It is possible to use a finely divided suspension of ruthenium. Preferably, however, the ruthenium is used supported on a carrier. Suitable carriers are for example aluminum oxide, silica gel, titanium dioxide, zirconium dioxide, magnesium aluminates and magnesium silicates. Preferred carriers are aluminum oxide and magnesium aluminate, in particular α-aluminas. The ruthenium is applied to the carrier in a conventional manner by impregnating the carrier with an aqueous solution of a ruthenium salt, such as ruthenium chloride or ruthenium nitrate, and subsequent drying with or without calcination.

The ruthenium concentration on the carrier is in general from 0.1 to 10% by weight, preferably from 0.5 to 5% by weight, in particular from 1 to 3% by weight. The supported ruthenium catalyst is in general activated in a stream of hydrogen, advantageously at from 180° to 250° C., in particular from 190° to 230° C., over for example 1-20 hours, preferably 1.5-10 hours.

In general, the space velocity over the catalyst is from 0.1 to 15 kg of 5-formylvaleric ester per kg of catalyst per hour, in particular from 1 to 10, especially from 4 to 10, kg of 5-formylvaleric ester per kg of catalyst per hour.

The reaction can be carried out batchwise, for example in a high pressure vessel. Advantageously, however, the reaction is carried out continuously, for example in a stirred vessel cascade, for example in from 2 to 5 vessels. It has been found to be advantageous to avoid back mixing during the reaction. For this reason it is particularly advantageous to pass a mixture of 5-formylvaleric ester and ammonia together with hydrogen over a fixed bed catalyst in a tubular reaction zone. It is very particularly advantageous to use the liquid phase procedure for this purpose. It comprises feeding an essentially upright tubular reaction zone (length diameter ratio for example from 8:1 to 50:1) containing the fixed bed catalyst from below with the 5-formylvaleric ester and liquid ammonia and also hydrogen and removing at the top of the tubular reaction zone the 6-aminocaproic ester together with ammonia, the water of reaction and any excess hydrogen.

In the preferred continuous process, the residence time in stage a follows from the weight hourly space velocity over the catalyst and the supply of ammonia. It is advantageously within the range from 0.5 to 20 minutes, preferably from 1 to 10, in particular 2 to 6, minutes.

The reaction mixture thus obtained contains besides hydrogen, which is removed after depressurization, the 6-aminocaproic ester, ammonia, and water formed in the course of the reaction, small amounts of byproducts such as caprolactam.

In stage b, the reaction medium ammonia is replaced by an inert aromatic hydrocarbon having a boiling point of from 80° to 240° C. which is liquid under the reaction conditions. Preferred aromatic hydrocarbons have a boiling point of from 110° to 200° C. and are preferably alkylbenzenes, in particular those which contain from 1 to 3 alkyl groups of up to 6 carbon atoms. Particular preference is given to alkylbenzenes having from 1 to 3 alkyl radicals of up to 4 carbon atoms in total. Suitable aromatic hydrocarbons are for example benzene, toluene, xylenes, ethylbenzene, diethylbenzene, trimethylbenzene, isopropylbenzene, propylbenzene and diisopropylbenzene. Toluene and xylenes are particularly advantageous. In general, from 2 to 20 kg, advantageously 4 to 15 kg, especially from 5 to 12 kg, of aromatic hydrocarbon are used per kg of 6-aminocaproic ester.

In general, the aromatic hydrocarbon is added in the stated amount to the exit stream from stage a before said exit stream is depressurized to atmospheric to remove the hydrogen. Excess ammonia is then distilled off. The distillation advantageously takes the form for example of stripping in a column using an inert gas such as nitrogen. The ammonia can also be distilled off at superatmospheric pressure. Alternatively, the exit stream from stage a is depressurized first, with hydrogen removal, before the aromatic hydrocarbon is added and the ammonia distilled off thereafter. Another possibility comprises initially depressurizing the mixture obtained from stage a to remove the hydrogen, distilling off the ammonia and mixing the remaining mixture of 6-aminocaproic ester and water with the aromatic hydrocarbon.

In general, the reaction in stage b is carried out in the presence of water of reaction; that is, in the presence of a molar amount of water based on the formylvaleric ester used in stage a.

In stage b, the water content of the mixture of aromatic hydrocarbon 6-aminocaproic ester and the water from the aminating hydrogenation is preferably adjusted to a level of from 1.1 to 10 moles of water per mole of 5-formylvaleric ester used in stage a by the addition of further water. Advantageously, the water content is set to from 1.5 to 6 moles, in particular from 2 to 4 moles, of water per mole of 5-formylvaleric ester used. The additional water is advantageously added after the ammonia has been separated off. In an advantageous procedure, the mixture of 6-aminocaproic ester, aromatic hydrocarbon and water is emulsified, preferably at from −10° to +20° C. This produces a mixture which contains an aromatic hydrocarbon reaction medium, a 6-aminocaproic ester, water, and a small amount of caprolactam. A typical composition is for example 65-95% by weight of an aromatic hydrocarbon, 6-20% by weight of 6-aminocaproic ester, 2-20% by weight of water and up to 1% by weight of caprolactam.

In stage c, this mixture is heated in liquid phase under superatmospheric pressure at 230°-350° C. to form caprolactam. Advantageously, the temperature is 260°-340° C. The temperature and the pressure conditions are chosen in such a way that the reaction mixture is always present in the liquid state. Advantageously, the pressure is set to 30-200 bar, in particular 40-110 bar.

Preferably, the residence time for the reaction is 5-60 minutes, advantageously 7-45 minutes, in particular 10-20 minutes.

The mixture of 6-aminocaproic ester, water and aromatic hydrocarbons is heated to the stated temperature under pressure and temperature conditions such that the reaction mixture is present in the liquid state. The reaction can be carried out batchwise, for example in a pressure vessel. Preferably, however, the reaction is carried out continuously, for example in a pressure vessel cascade, for example in 2-4 consecutive pressure vessels. It is particularly advantageous to carry out the reaction in a tubular reaction zone having a length:diameter ratio of for example from 100:1 to 1000:1.

In stage d, the reaction mixture obtained, which contains an aromatic hydrocarbon, caprolactam, water, the alcohol corresponding to the ester, and a small amount of 6-aminocaproic ester, is treated to isolate the caprolactam. In general, the reaction mixture is subjected to fractional distillation to isolate the caprolactam. The aromatic hydrocarbon recovered in the course of the fractional distillation is advantageously recycled. In a preferred procedure, the caprolactam is extracted from the aromatic hydrocarbon with water. Advantageously, the extraction is carried out in countercurrent in known apparatus, for example mixer settlers, stirred disk columns or sieve plate columns with or without pulsation. Advantageously, the extraction is carried out at from 20° to 80° C. It is also advantageous to purify a bleed stream of recovered aromatic hydrocarbon by a distillation before reuse.

The caprolactam obtainable by the process of the present invention is suitable for preparing polycaprolactam.

The process according to the present invention is illustrated by the following Examples:

EXAMPLE 1

A vertical tube reactor (diameter: 9 mm, fill level: 37 cm, oil-heated jacket) was packed with 17.2 g of catalyst comprising 2.78% of ruthenium on aluminum oxide in the form of 1.5 mm extrudates (catalyst preparation by diffusion impregnation with aqueous ruthenium chloride solution and drying at 70° C.). To activate the catalyst, hydrogen was passed through at a rate of 20 standard l/h and the temperature was raised from 100° to 220° C. in the course of 7 hours and then maintained at 220° C. for 6 hours.

After cooling down to 128° C., a stream of 100.8 ml of methyl 5-formylvalerate (purity: 99%; 102.2 g, 0.710 mol) and 280 ml (168 g, 9.9 mol) of liquid ammonia per hour was pumped upward through the reactor under a pressure of 98 bar together with 66 standard l/h (2.9 mol) of hydrogen.

The exit stream was depressurized to atmospheric via a pressure control valve and taken up in 1035 ml of xylene per hour, and the xylene mixture was passed downward at 40°·C. through a column (15 cm in length and packed with 5 mm glass rings) through which nitrogen was blown in countercurrent at a rate of 20 l/h. At the base of the column, a two-phase mixture was obtained at a rate of 1019 g per hour. After a sample had been homogenized with methanol, quantitative analysis by gas chromatography revealed a concentration of 8.6% of methyl 6-aminocaproate and 0.3% of caprolactam, corresponding to hydrogenation yields of 85.1% of methyl 6-aminocaproate and 3.8% of caprolactam.

The two phases were separated, and 26 g/h (1.4 mol) of water were added to the aqueous phase (19.8 g/h). The aqueous phase and the xylene phase were metered at hourly rates of 8.25 ml (8.09 g) and 260 ml (228.9 g) respectively into a 70 ml tube reactor (2.2 mm in diameter) at 100 bar and 270° C.

The exit stream collected over 2.55 hours was concentrated in a rotary evaporator. The residue of 52.3 g contained 72.9% of caprolactam and 3.0% of methyl 6-aminocaproate according to quantitative analysis by gas chromatography. The total yield of caprolactam was 81.9%, based on methyl 5-formylvalerate.

EXAMPLE 2

A vertical tube reactor (diameter: 9 mm, fill level: 37 cm, oil-heated jacket) was packed with 14.0 g of catalyst comprising 2.78% of ruthenium on aluminum oxide in the form of 1.5 mm extrudates (catalyst preparation by diffusion impregnation with aqueous ruthenium chloride solution and drying at 70° C.). To activate the catalyst, a mixture of nitrogen and hydrogen was passed through at a rate of 60 standard l/h and the temperature was raised from 20° to 200° C. in the course of 6 hours and then maintained at 200° C. for 6 hours.

After cooling down to 126° C., a stream of 85.6 ml of methyl 5-formylvalerate (87.7 g, 0.609 mol) and 368 ml (221 g, 13 mol) of liquid ammonia per hour was pumped upward through the reactor under a pressure of 99 bar together with 52 standard l/h (2.3 mol) of hydrogen.

The exit stream was depressurized to atmospheric via a pressure control valve and taken up in 336 ml of xylene per hour, and the xylene mixture was passed downward at 40° C. through a column (15 cm in length and packed with 5 mm glass rings) through which nitrogen was blown in countercurrent at a rate of 20 l/h. At the base of the column, a two-phase mixture was collected at a rate of 376.6 g per hour and found, by quantitative gas chromatography analysis, to contain 21.6% of methyl 6-aminocaproate and 0.6% of caprolactam, corresponding to hydrogenation yields of 92.2% and 3.3% respectively.

The two-phase mixture was emulsified in a jacketed flask temperature-controlled to 0° C., and the emulsion was pumped at a rate of 359.0 ml per hour through a 70 ml tube reactor (2.2 mm in diameter) at a pressure of 75 bar and 270° C. The exit stream collected over 1.83 h (750.1 g) was concentrated in a rotary evaporator. The residue of 104.2 g was found by quantitative gas chromatography to contain 90.1% of caprolactam and 0.34% of methyl 6-aminocaproate. The total yield of caprolactam was 84.4%, based on methyl 5-formylvalerate.

We claim:

1. A process for preparing caprolactam, comprising the following steps:

(a) reacting a 5-formylvaleric ester with liquid ammonia as reaction medium and hydrogen in the presence of a ruthenium catalyst in liquid phase at from 80° to 140° C. under a hydrogen partial pressure of from 40 to 100 bar, (b) replacing the reaction medium ammonia by an aromatic hydrocarbon having a boiling point of from 80° to 240° C. which is liquid under the reaction conditions, (c) heating the resulting mixture in liquid phase under superatmospheric pressure at 230°-350° C. to form caprolactam, and (d) isolating caprolactam from the resulting reaction mixture.

2. A process as claimed in claim 1, wherein from 1.2 to 3.6 kg of ammonia are used per kg of 5-formylvaleric ester.

3. A process as claimed in claim 1, wherein a supported catalyst containing from 0.1 to 10% by weight of ruthenium is used.

4. A process as claimed in claim 1, wherein a temperature of from 100° to 135° C. is maintained in stage a.

5. A process as claimed in claim 1, wherein a residence time of from 1 to 10 minutes is maintained in stage a.

6. A process as claimed in claim 1, wherein a weight hourly space velocity of from 0.1 to 15 kg of 5-formylvaleric ester per kg of catalyst per hour is maintained.

7. A process as claimed in claim 1, wherein the 5-formylvaleric ester is passed with liquid ammonia and hydrogen over a fixed bed supported ruthenium catalyst in a tubular reaction zone in a liquid phase procedure with substantial avoidance of back mixing.

8. A process as claimed in claim 1, wherein an aromatic hydrocarbon having a boiling point of from 110° to 200° C. which is liquid under reaction conditions is used in stage b.

9. A process as claimed in claim 1, wherein from 2 to 20 kg of aromatic hydrocarbons are used per kg of 6-aminocaproic ester.

10. A process as claimed in claim 1, wherein the reaction mixture of stage a is mixed with an aromatic hydrocarbon and ammonia is distilled off.

11. A process as claimed in claim 1, wherein ammonia is distilled out of the reaction mixture from stage a and the remaining mixture is mixed with an aromatic hydrocarbon.

12. A process as claimed in claim 1, wherein a water content of from 1.1 to 10 moles per mole of 5-formylvaleric ester, based on the amount used in stage a, is set in stage b.

13. A process as claimed in claim 1, wherein the mixture of aromatic hydrocarbon, 6-aminocaproic ester and water is emulsified at from −10° to +20° C.

14. A process as claimed in claim 1, wherein a temperature of from 260° to 340° C. is maintained in stage d.

15. A process as claimed in claim 1, wherein a pressure of from 40 to 110 bar is maintained in stage c.

16. A process as claimed in claim 1, wherein a residence time of from 5 to 60 minutes is maintained in stage c.

17. A process as claimed in claim 1, wherein caprolactam is isolated by extraction with water in stage d.

* * * * *